US 9,277,895 B2

(12) United States Patent
Hara et al.

(10) Patent No.: US 9,277,895 B2
(45) Date of Patent: Mar. 8, 2016

(54) X-RAY CT APPARATUS

(71) Applicant: Rigaku Corporation, Akishima (JP)

(72) Inventors: Yukihiro Hara, Hino (JP); Kiyoshi Akiyama, Tachikawa (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 223 days.

(21) Appl. No.: 14/063,167

(22) Filed: Oct. 25, 2013

(65) Prior Publication Data

US 2014/0126689 A1 May 8, 2014

(30) Foreign Application Priority Data

Nov. 7, 2012 (JP) ................................. 2012-245080
Aug. 22, 2013 (JP) ................................. 2013-172085

(51) Int. Cl.
*A61B 6/04* (2006.01)
*A61B 6/03* (2006.01)
*A61B 6/00* (2006.01)

(52) U.S. Cl.
CPC .............. *A61B 6/0407* (2013.01); *A61B 6/032* (2013.01); *A61B 6/035* (2013.01); *A61B 6/4405* (2013.01); *A61B 6/508* (2013.01)

(58) Field of Classification Search
CPC ........... A61B 6/035; A61B 6/04; A61B 6/032
See application file for complete search history.

(56) References Cited

U.S. PATENT DOCUMENTS

| 5,097,497 A * | 3/1992 | Deucher et al. ............... 378/204 |
| 7,453,980 B1 * | 11/2008 | Gilevich et al. ................. 378/57 |
| 2005/0169422 A1 * | 8/2005 | Ellenbogen ..................... 378/57 |
| 2006/0269165 A1 | 11/2006 | Viswanathan |
| 2011/0282181 A1 | 11/2011 | Wang et al. |

FOREIGN PATENT DOCUMENTS

| DE | 44 42 690 A1 | 6/1996 |
| JP | 2006-340963 A | 12/2006 |

* cited by examiner

*Primary Examiner* — Hoon Song
(74) *Attorney, Agent, or Firm* — Buchanan Ingersoll & Rooney PC

(57) ABSTRACT

An X-ray CT apparatus for obtaining an internal image of a test subject by using X-rays. The X-ray CT apparatus has: an X-ray generator; an X-ray detector; a first casing for enclosing the X-ray generator and the X-ray detector; a test-subject table; a first table transporting mechanism for transporting the test-subject table between a first table position and a second table position, the first table position being a position where the main portion of the test-subject table receives X-rays from the X-ray generator, and the second table position being a position where the main portion of the test-subject table is on the outside of the first casing; and a second table transporting mechanism capable of vertically transporting the test-subject table. The first table transporting mechanism and the second table transporting mechanism operate in association with each other.

7 Claims, 9 Drawing Sheets

X-RAY CT APPARATUS

BACKGROUND OF THE INVENTION

1. Field of the Invention

The present invention relates to an X-ray CT (computer tomography) apparatus, which is a CT apparatus making use of X-rays.

2. Description of the Related Art

X-ray CT apparatuses are widely used, for example, in the field of medicine in order to obtain cross-sectional or three-dimensional images of the interior of a test subject. In recent years, there has been increasing demand for the use of advanced diagnostic apparatuses having the ability to perform CT scans and the like in veterinary hospitals due to the influence of the "pet boom." However, CT apparatuses intended for veterinary hospitals for use on small and medium-sized animals are not generally used at present, and currently they are substituted with CT apparatuses for use on humans. However, because CT apparatuses for use on humans are large, a dedicated X-ray irradiation chamber having a large open space is necessary in order to install such a CT apparatus. Because of this, there has been only a moderate increase in the use of CT apparatuses in veterinary hospitals.

A conventional example of an X-ray CT apparatus in which small test subjects serve as measurement objects is disclosed in Patent Citation 1. An X-ray CT apparatus having a door provided to a side surface of a housing containing an X-ray generator and an X-ray detector is disclosed in Patent Citation 1. When a CT measurement is performed on a test subject such as a small animal or the like using this CT apparatus, the door is opened to place the test subject in a specific position inside the housing, and the X-ray generator and the X-ray detector are operated to perform the CT measurement.

PRIOR ART DOCUMENTS (Patent Citation 1) Japanese Laid-open Patent Publication No. 2006-340963

In a conventional X-ray CT apparatus, however, when the measurer places the test subject in a specific position inside the CT apparatus, the measurer must have the uncomfortable posture of inserting his/her body part (for example, an arm) into the housing, leading to extremely great physical strain. It is especially an appreciable physical strain for female veterinary doctors and nurses.

SUMMARY OF THE INVENTION

The present invention was devised in view of the problems encountered in the conventional apparatus described above, and an object thereof is to provide an X-ray CT apparatus whereby the test subject can be set (i.e., arranged) precisely, simply, and quickly in a specific measurement position.

The X-ray CT apparatus according to the present invention is the X-ray CT apparatus for obtaining an internal image of a test subject by using X-rays, the X-ray CT apparatus comprising: X-ray generation means for generating X-rays irradiated on the test subject; X-ray detection means for detecting the X-rays that have passed through the test subject; rotary drive means for simultaneously rotating the X-ray generation means and the X-ray detection means about the center line (occasionally referred to as "the center line of rotation of the X-rays" hereinbelow); a first casing for enclosing the X-ray generation means and the X-ray detection means; a test-subject table on which the test subject is placed; a first table transporting mechanism for transporting the test-subject table between a first table position and a second table position, the first table position being a position where the main portion of the test-subject table receives the X-rays generated by the X-ray generation means, and the second table position being a position where the main portion of the test-subject table is on the outside of the first casing; and a second table transporting mechanism for transporting the test-subject table closer to or farther from the center line of rotation of the X-rays.

In the X-ray CT apparatus according to the present invention, the measurer can set (i.e., arrange) and remove the test subject on and from the test-subject table in the second table position, which is a position outside the first casing, because the first table transporting mechanism is configured to transport the test-subject table between the first table position, which is a position for receiving X-rays, and the second table position, which is a position outside the first casing. Further, the test subject on the test-subject table may be placed consistently and precisely in the first table position by the action of the first table transporting mechanism.

Therefore, the task of setting (arranging) the test subject in a specific position inside the first casing can be performed more simply, more quickly, and more precisely according to the present invention than with the conventional CT apparatus, in which the test subject is arranged inside the casing through an aperture that becomes visible after the door provided to a side surface of the casing is opened.

Moreover, because the position of the test-subject table in relation to the center line of rotation of the X-rays is adjusted in the present invention by the second table transporting mechanism, it is possible to place the test subject consistently in a given position in relation to the X-rays so that the physical axis of the test subject conforms to the center line of rotation of the X-rays even in a case in which test subjects are provided in varying sizes. A consistently stable, highly reliable CT measurement can thereby be performed on test subjects of differing sizes. The phrase "the physical axis of the test subject conforms to the center line of rotation of the X-ray" includes cases of perfect conformity as well as cases in which the reliability of the result of the X-ray CT measurement deviates to an extent at which the reduction is still within a permissible level.

The X-ray CT apparatus according to the present invention may have a second casing for enclosing the second table position. The second casing may have a pair of doors that move open or closed in order to open up or close off the path on which the test-subject table is transported by the first table transporting mechanism.

According to this aspect of the present invention, the second table position, which is a position where the measurer takes the test subject in and out, may be enclosed by the second casing. Closing the pair of doors allows the interior and exterior of the second casing to be spatially blocked off and the X-rays to be confined within. As a result, the operator need not follow the procedure of going outside upon introducing the X-ray CT apparatus into the dedicated X-ray chamber, but rather can perform the measurement operation safely while in the immediate vicinity of the X-ray CT apparatus.

A window for observing the interior may be provided to either one or both of the pair of doors. This allows measurer to observe, through the window, the condition of a test subject being transported or the condition of a test subject being subjected to a CT measurement.

The X-ray CT apparatus according to the present invention may have transporting means whereby the test-subject table on which the test subject is placed is transported from the second table position to the first table position by the first table transporting mechanism, and varying means whereby the distance of the test subject from the center line of rotation of the X-ray generation means and the X-ray detection means is varied by the second table transporting mechanism in accordance with the size of the test subject.

The "transporting means" and the "varying means" may both be implemented, for example, using a CPU in a computer, and software that causes the CPU to function as function-implementing means.

According to this aspect of the present invention, the first table transporting mechanism and the second table transporting mechanism may be efficiently linked and operated by the combined use of the "transporting means" and the "varying means."

The X-ray CT apparatus according to the present invention may have: laser pointer means for indicating a position by laser light; a window provided to the first casing or the second casing in order to observe the position indicated by the laser pointer means; and input means for inputting data. The varying means for varying the distance of the test subject may vary, by the second table transporting mechanism, the distance of the test subject from the center line of rotation of the X-ray generation means and the X-ray detection means in accordance with the data input from the input means.

According to this aspect of the present invention, the measurer may evaluate the extent to which the position of the test subject deviates from the proper position by observing the laser light of the laser pointer means and the test subject. Once the measurer inputs the appropriate data on the basis of that evaluation using the input means, the "varying means" can consistently adjust the distance of the test-subject table in relation to the X-ray generation means to a proper level in accordance with the input data.

The X-ray CT apparatus according to the present invention may have input means for inputting data, and means whereby the distance of the test subject in relation to the center line of rotation of the X-ray generation means and the X-ray detection means is determined by X-ray fluoroscopy. The varying means for varying the distance of the test subject may vary, by the second table transporting mechanism, the distance of the test subject from the center line of rotation of the X-ray generation means and the X-ray detection means in accordance with the data determined by X-ray fluoroscopy.

As referred to herein, the "means whereby the distance of the test subject is determined by X-ray fluoroscopy" may be implemented, for example, using a unit comprising an X-ray generator, an X-ray detector, a CPU, and software. The "varying means" can be implemented, for example, using a CPU of a computer, and software that causes the CPU to function as function-implementing means.

According to this aspect of the present invention, the measurer can evaluate the extent to which the position of the test subject deviates from the proper position by performing X-ray fluoroscopy. Once the measurer inputs the appropriate data on the basis of that evaluation using the input means, the "varying means" may consistently adjust the distance of the test-subject table in relation to the center line of rotation of the X-rays to a proper level in accordance with the input data.

The X-ray CT apparatus according to the present invention may have a third table transporting mechanism for transporting the test-subject table to a third table position, which is a position even farther from the first casing than the second table position.

According to this aspect of the present invention, because the test-subject table may be brought out to a separate position even farther from the first casing than the second table position, the test subject may easily be placed on the test-subject table even in cases in which the size of the test subject is much larger.

In the X-ray CT apparatus according to the present invention, the test-subject table can have a curved cross-sectional shape in which the surface for receiving the test subject is recessed. This shape is a so-called trough-type shape. According to this configuration, the test subject is positioned on the lowest portion of the curved shape of the test-subject table, resulting in the test subject being placed consistently in a given position. The test-subject table may be formed using a translucent material, i.e., a material in which the underside may be seen through.

Effects of the Invention

In the X-ray CT apparatus according to the present invention, the measurer may set (i.e., arrange) and remove the test subject on and from the test-subject table in the second table position, which is a position outside the first casing, because the first table transporting mechanism is configured to transport the test-subject table between the first table position, which is a position for receiving X-rays, and the second table position, which is a position outside the first casing. Further, the test subject on the test-subject table is placed consistently and precisely in the first table position by the action of the first table transporting mechanism.

Therefore, the task of setting (i.e., arranging) the test subject in a specific position inside the first casing may be performed more simply, more quickly, and more precisely according to the present invention than with the conventional CT apparatus, in which the test subject is arranged inside the casing through an aperture that becomes visible after the door provided to a side surface of the casing is opened.

Moreover, because the distance of the test-subject table from the center line of rotation of the X-rays is adjusted in the present invention by the second table transporting mechanism, it is possible to place the central portion of the test subject consistently in a given position in relation to the X-rays even in a case in which test subjects are provided in varying sizes. A consistently stable, highly reliable CT measurement may thereby be performed on test subjects of differing sizes.

DESCRIPTION OF THE PREFERRED EMBODIMENTS

Figure 1:
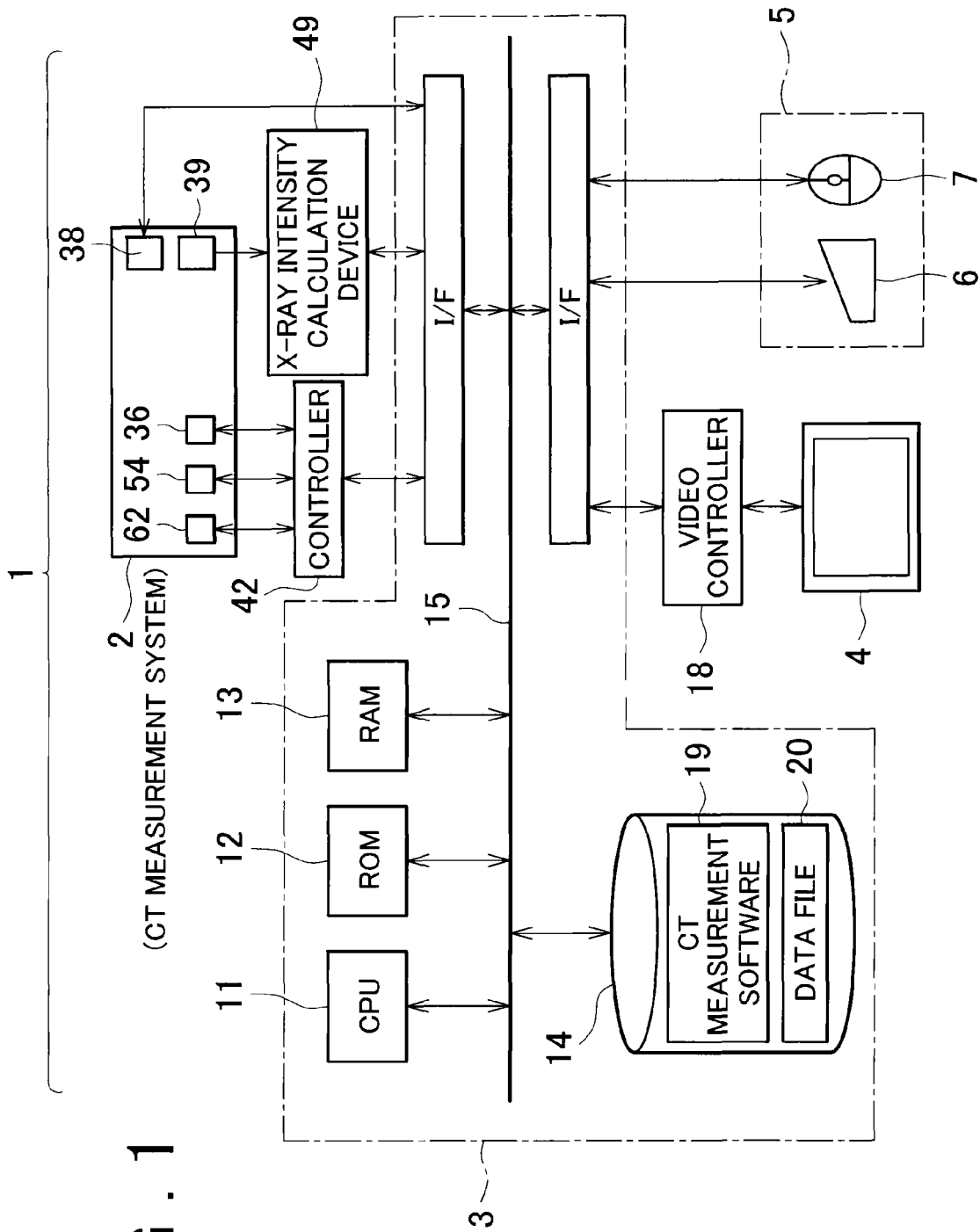
FIG. 1 is a block diagram of an embodiment of an X-ray CT apparatus according to the present invention.

The X-ray CT apparatus according to the present invention is described hereinbelow on the basis of embodiments. As shall be apparent, the present invention is not limited to these embodiments. In the drawings accompanying the specification, the configurational elements may be illustrated with different ratios from the actual elements in order to make characteristic portions easier to understand.

FIG. 1 shows the entire configuration of an X-ray CT apparatus 1 according to the present invention using a block diagram. In FIG. 1, the X-ray CT apparatus 1 has: a CT measurement system 2, which is a mechanical measurement system; a control device 3 configured to include a CPU (central processing unit); an image display device 4 configured using a display such as a liquid crystal display device or the like; and an input device 5, which is a device for inputting data. The input device 5 includes a keyboard 6 and a mouse 7 in the present embodiment.

The control device 3 has a CPU 11, a ROM (read-only memory) 12, a RAM (random access memory) 13, a memory 14, and a bus 15 to connect these units together. The ROM 12 and the RAM 13 constitute internal memory. The memory 14 is external memory, and is configured using, for example, a hard disk, a CD (compact disk), a DVD (digital video disk), or the like. A CT measurement software 19, which is application software for implementing a CT measurement in collaboration with the CPU 11, and a data file 20, which is a region for storing a variety of data in memory, are stored within the memory 14.

The image display device 4 displays an image on the display screen on the basis of the output signal of a video controller 18. The video controller 18 inputs image data transmitted from the control device 3, converts that image data into an image signal in accordance with a specific procedure, and transmits the image signal to the image display device 4. The image data is thereby displayed as an image on the screen of the image display device 4.

Figure 2:
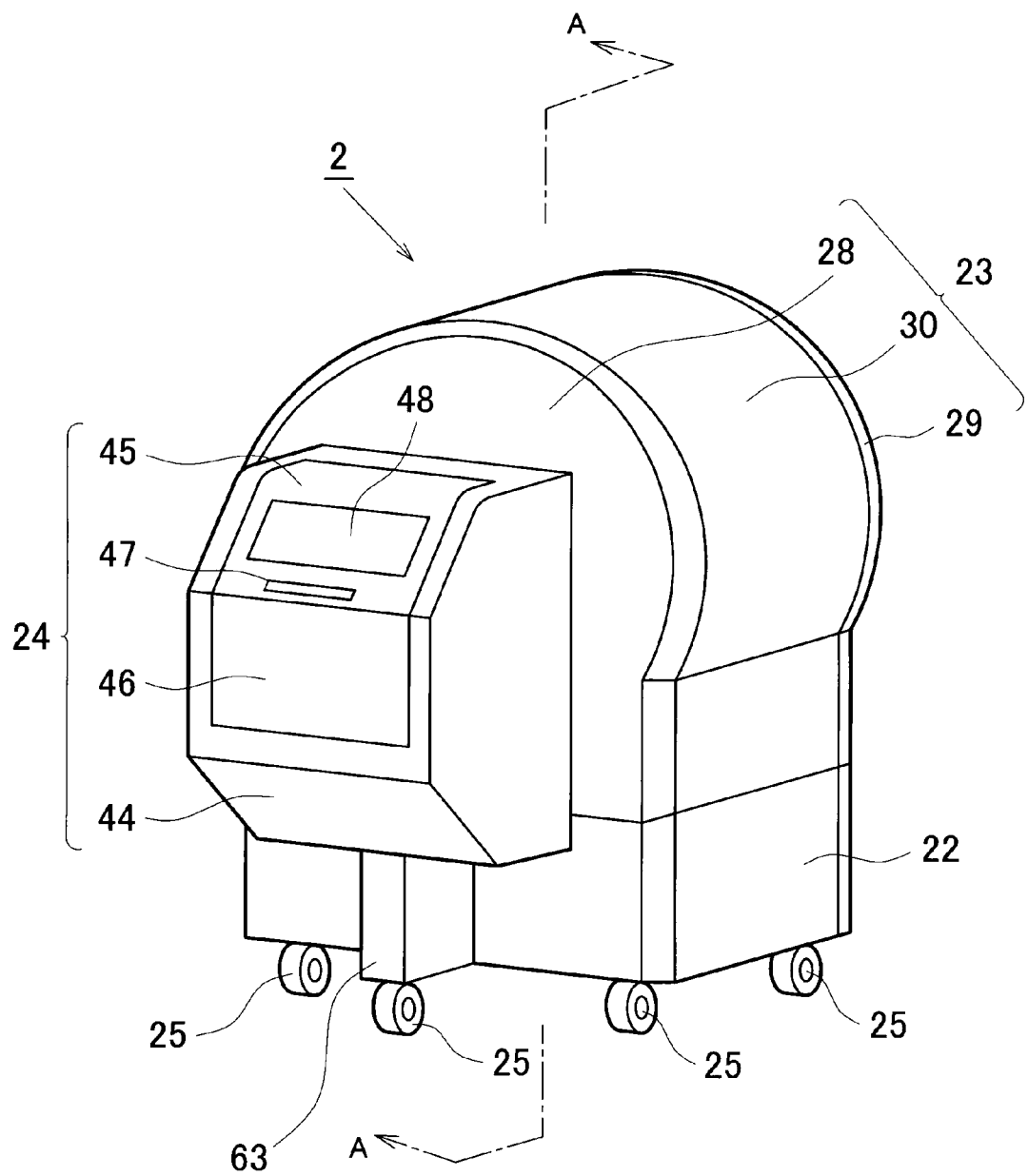
FIG. 2 is a perspective view showing an embodiment of a CT measurement system, which is a principal part of FIG. 1.

The CT measurement system 2 has the exterior shape shown in FIG. 2. The CT measurement system 2 has a base 22, a first casing 23 installed over the base 22, and a second casing 24 linked to the base 22 and the first casing 23. Casters 25 are provided on the bottom surface of the base 22 to allow the entire CT measurement system 2 to be moved. The casters 25 have a structure which can take on two states, which are the rolling-enabled state and the rolling-disabled state. The casters 25 are set to the rolling-disabled state in a case in which the CT measurement system 2 is installed in a fixed position in a specific area on the floor.

(First Casing)

Figure 3:
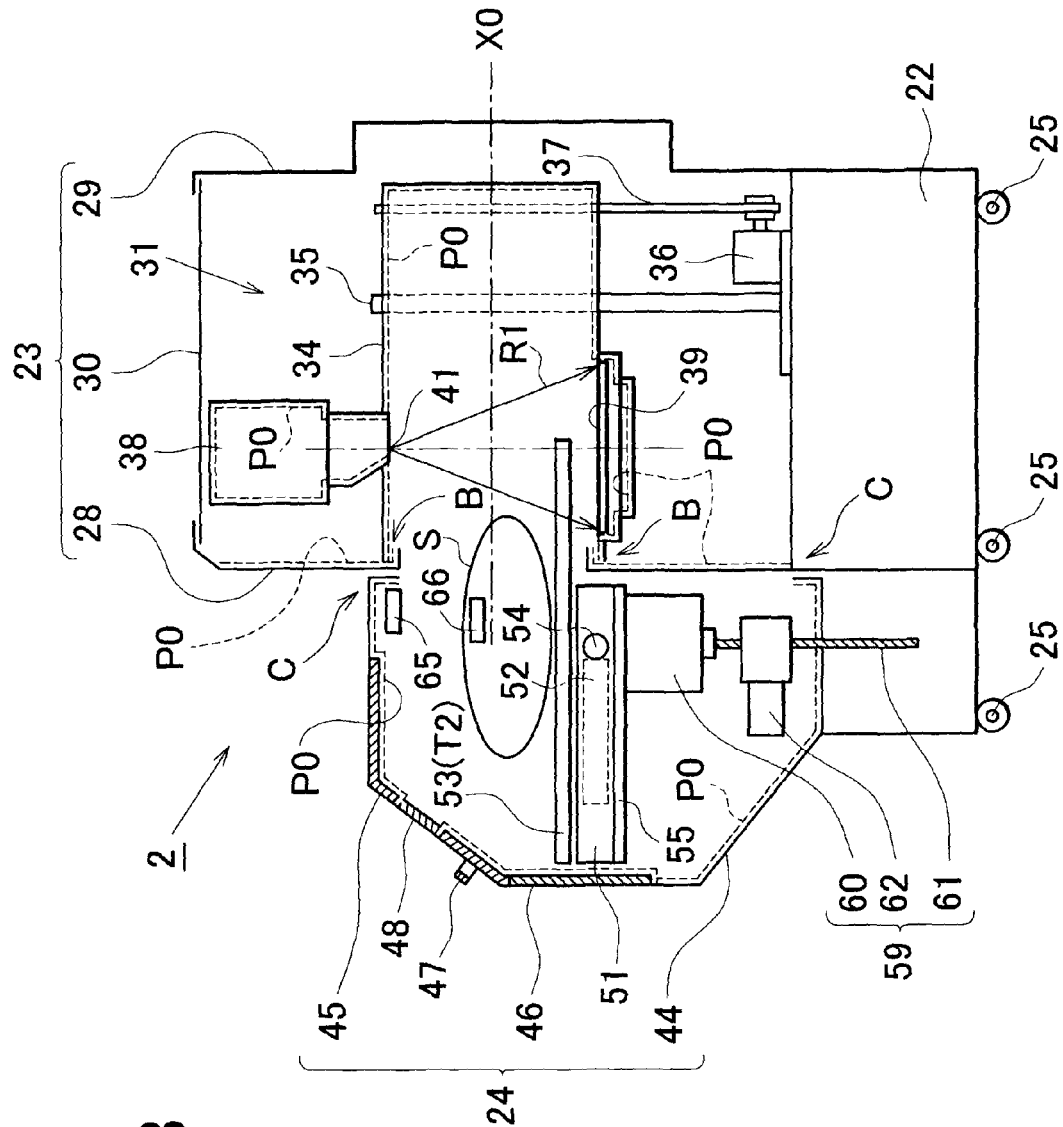
FIG. 3 is a cross-sectional view along line A-A of FIG. 2.
Figure 4:
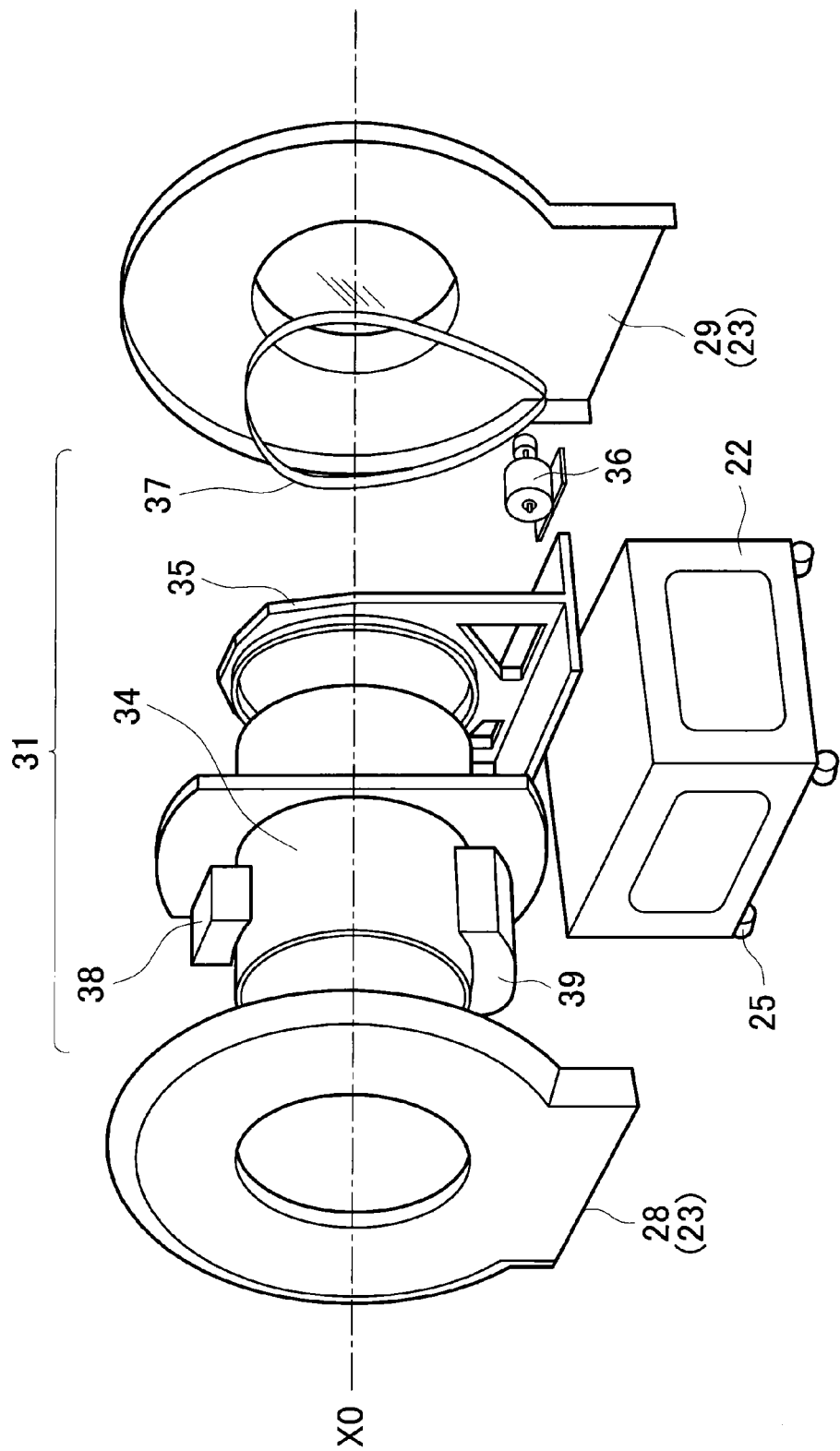
FIG. 4 is an exploded perspective view showing an embodiment of a CT optical system, which is a principal part of FIG. 3.

The first casing 23 has a front-surface plate 28, a back-surface plate 29, and a drum plate 30. FIG. 3 shows a cross-sectional structure along line A-A of FIG. 2. In FIG. 3, a CT optical system 31 is housed inside the first casing 23, i.e., the first casing 23 encloses the CT optical system 31. As shown in FIG. 4, the CT optical system 31 has: a rotating drum 34; a supporting member 35 for rotatably supporting the rotating drum 34; a motor 36, which is a power source for rotating the rotating drum 34; and a belt 37 as a power transmitting means for transmitting the rotation of the output shaft of the motor 36 to the rotating drum 34. The motor 36 is connected to the CPU 11 in the control device 3 through a controller 42 in FIG. 1.

An X-ray generator 38 is fixed to a location on the external peripheral surface of the rotating drum 34 in a portion close to the front-surface plate 28 of the first casing 23. Although any fixing method may be used, the X-ray generator 38 is fixed without any gap so that no X-rays leak out. The X-ray emission surface of the X-ray generator 38 is directed into the rotating drum 34. The X-ray generator 38 generates X-rays in accordance with the supply of a high voltage. The X-ray generator 38 emits an X-ray R1 from an X-ray emission window 41 to the exterior. The X-ray R1 travels while spreading in a conical shape or a square pyramidal shape (i.e., three-dimensionally). The signal input terminal of the X-ray generator 38 is connected to the CPU 11 in the control device 3, as shown in FIG. 1.

The X-ray generator 38 is configured so that no X-rays pass through to the exterior from any portion other than the X-ray emission surface, i.e., the X-ray generator 38 has a structure that has an inherent shielding function against X-rays. Although such a structure with an inherent shielding function may be attained by various configurations, the structure with an inherent shielding function is implemented in the present embodiment by covering the entire X-ray generator 38 with a lead plate P0, as shown in FIG. 3.

In FIG. 3, a two-dimensional X-ray detector 39 is fixed to another location on the external peripheral surface of the rotating drum 34 at a position opposite the X-ray generator 38. Although the X-ray detector 39 can also be fixed by any method, the X-ray detector 39 is fixed without any gap so that no X-rays leak out, in the same manner as was the case with the X-ray generator 38. The X-ray detection surface of the two-dimensional X-ray detector 39 is directed into the rotating drum 34.

The X-ray detector 39 is also configured to have an inherent shielding function against X-rays, in the same manner as the X-ray generator 38. Specifically, the structure with an inherent shielding function is implemented by covering the entire X-ray detector 39 with a lead plate P0 as shown in FIG. 3, in the same manner as was the case with the X-ray generator 38.

The two-dimensional X-ray detector 39 is an X-ray optical element for receiving X-rays in two dimensions (i.e., in a plane) and outputting an electrical signal that corresponds to the intensity of the X-rays received by the individual regions within a two-dimensional region. Such a two-dimensional X-ray detector 39 may be formed using, for example, a two-dimensional CCD (charge-coupled device) sensor, a photon-counting two-dimensional sensor, or the like. The signal output terminal of the X-ray detector 39 is connected to the CPU 11 in the control device 3 through an X-ray intensity calculation device 49, as shown in FIG. 1.

When the motor 36 in FIG. 3 is operated, the rotational power is transmitted to the rotating drum 34 by the belt 37, and the rotating drum 34 rotates about a center axis line X0 at a specific rotation speed. Due to the rotation of the rotating drum 34, the X-ray generator 38 and the X-ray detector 39 rotate about the center axis line X0 at a specific rotation speed while maintaining a state of opposition to each other.

In the rotating drum 34, the end part of the first casing 23 on one side of the front-surface plate 28 is an open end, and the end part on the opposite side is a closed end. Although the rotating drum 34 of the present embodiment is cylindrical, it is also acceptable for the rotating drum 34 to be formed in the shape of a square or rectangular tube, an elliptic cylinder, a stretched cylinder, or another desired solid shape as necessary. The rotating drum 34 is formed of a metal composed primarily of Fe (iron), a fiber reinforced plastic (FRP), or the like. The entire internal peripheral surface of the rotating drum 34 is lined with (i.e., has attached to the back) a lead plate P0 in order to prevent X-rays from passing through the rotating drum 34 and leaking to the exterior. The lead plate P0 is formed using lead or a lead alloy.

The rotating drum 34 may also be lined with an X-ray-blocking heavy metal (a metal having a specific weight of 4 to 5 or greater) or an alloy containing the heavy metal, instead of the lead plate P0. The leaking of X-rays in the rotating drum 34 may also be prevented by forming the entire rotating drum 34 from lead, a lead alloy, a heavy metal, an alloy containing a heavy metal, or the like. The X-ray generator 38 and the X-ray detector 39 are enclosed in an exterior frame. The internal peripheral surface of the exterior frame is lined with a lead plate or the like in order to prevent the leaking of the X-rays.

As described above, the CT optical system 31 rotating about the center axis line X0 has an X-ray shielding function, which is a function for preventing the leaking of the X-rays to the exterior. Because the CT optical system 31 has an X-ray shielding function in this manner in the present embodiment, it is not necessarily required for the first casing 23 that encloses the CT optical system 31 to be provided with an X-ray shielding function by lining the casing with a lead plate, or the like. However, for the front-surface plate 28 of the first casing 23, which is a member that fits with the open end of the rotating drum 34, it is preferable at least for the portion that fits with the rotating drum 34 to be provided with the X-ray shielding function by lining that portion with a lead plate, or the like. This is because such a fitting part has a structure in which gaps can easily form.

(Second Casing)

Referring again to FIG. 2, the second casing 24 is a casing projecting in front of the first casing 23. The second casing 24 has a main casing unit 44, an upper door 45 as a first door provided to the upper part of the main casing unit 44, and a lower door 46 as a second door provided to the lower part of the main casing unit 44. A handle 47 is provided on the front surface of the upper door 45. A window 48 to be used when the measurer observes the interior is provided to the central part of the upper door 45.

Figure 5:
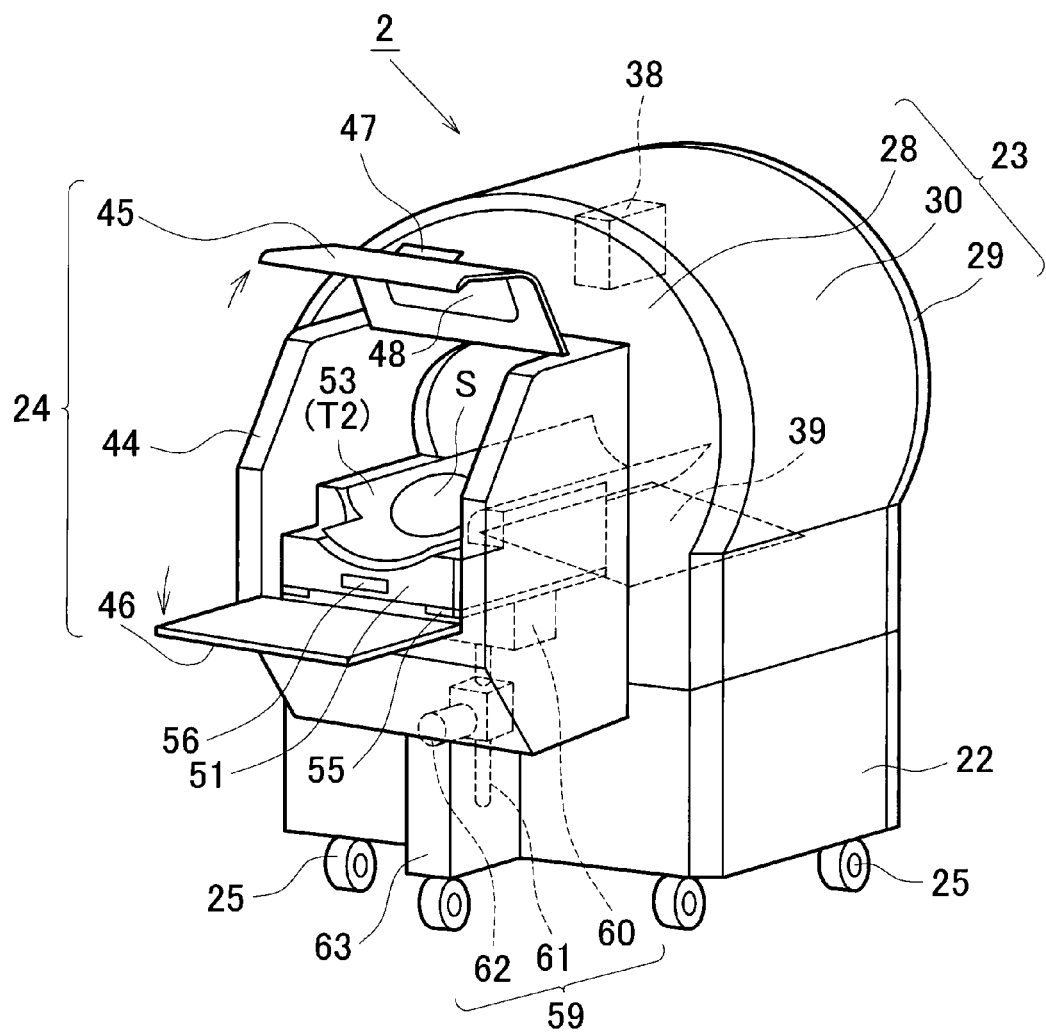
FIG. 5 is a perspective view showing one usage configuration of the CT measurement system shown in FIG. 2.

As shown in FIG. 5, the upper door 45 can move rotatably about the upper edge part. The lower door 46 can move rotatably about the lower edge part. In FIG. 2, the upper door 45 and the lower door 46 are both in a closed state, and the lower edge part of the upper door 45 and the upper edge part of the lower door 46 are in contact or fitted with each other without any gap. In FIG. 5, the upper door 45 and the lower door 46 are both in an opened state. When the upper door 45 and the lower door 46 are both in an opened state, the front surface of the second casing 24 is in a widely opened state.

The upper door 45 can move open or closed, i.e., move rotatably, independently and regardless of the lower door 46. In a case in which the upper door 45 is in a closed state and the lower edge part of the upper door 45 is in contact or fitted with the upper edge part of the lower door 46, the lower door 46 is constrained by the upper door 45 and cannot move open or closed, i.e., cannot move rotatably. In a case in which the upper door 45 is caused to move to open upward, the lower door 46 maintains a closed position. In a case in which the measurer desires to move the lower door 46 to open downward, the measurer grasps the upper edge part of the lower door 46 and pulls the upper edge downward.

In FIG. 3, the main casing unit 44, the upper door 45, and the lower door 46 of the second casing 24 are formed using a metal primarily composed of Fe (iron), a fiber reinforced plastic (FRP), or the like. The entire internal peripheral surface of the main casing unit 44, the upper door 45, and the lower door 46 are lined with (i.e., have attached to the back) lead plates P0 in order to prevent X-rays from passing through the second casing 24 and leaking to the exterior. The lead plates P0 are formed using lead or a lead alloy. The window 48 for observation of the interior is formed using a transparent member opaque to X-rays, for example, leaded glass.

The main casing unit 44, the upper door 45, and the lower door 46 may also be lined with an X-ray-blocking heavy metal (a metal having a specific weight of 4 to 5 or greater) or an alloy containing the heavy metal, instead of the lead plates P0. The leaking of X-rays in the second casing 24 may also be prevented by forming the entire main casing unit 44, the entire upper door 45, and the entire lower door 46 from lead, a lead alloy, a heavy metal, an alloy containing a heavy metal, or the like.

As described above, the escape of X-rays to the exterior of the CT measurement system 2 in a case in which the X-rays are emitted from the X-ray generator 38 and a CT measurement is performed can be prevented in the present embodiment by giving an X-ray shielding function to each part of the main casing unit 44, the upper door 45, and the lower door 46 of the second casing 24 in combination with giving an X-ray shielding function to the CT optical system 31 inside the first casing 23.

In the present embodiment, the area of lead used for implementing an X-ray shielding function can be small because a portion of the CT optical system 31, which is a small configurational element portion for generating X-rays, is given an X-ray shielding function, and the first casing 23, which is a large configurational element portion, is not given the X-ray shielding function. Therefore, the weight of the CT measurement system 2 can be greatly reduced.

In the present embodiment, in the connecting portions B between the open end of the rotating drum 34 of the CT optical system 31 and the front-surface plate 28 of the first casing 23, the end parts of the front-surface plate 28 and the end parts of the rotating drum 34 were constructed with a mutually overlapping configuration by folding the end edge of the front-surface plate 28. In the connecting portions C between the front-surface plate 28 of the first casing 23 and the main casing unit 44 of the second casing 24, the edge parts of the front-surface plate 28 and the edge parts of the main casing unit 44 were constructed with a mutually overlapping configuration by folding the end edge of the main unit portion 44.

It is easy for a gap to develop in the connecting portion between the CT optical system 31, the first casing 23, and the second casing 24. When a gap develops, it is possible for X-rays to escape through the gap. In the present embodiment, each part of the CT optical system 31, the first casing 23, and the second casing 24 was given an X-ray shielding function by a lead plate lining, and the edges of the parts were configured to overlap each other. Therefore, the lead plate lining at the connecting portion between the CT optical system 31, the first casing 23, and the second casing 24 was constructed with an overlapping configuration. As a result, the leaking of the X-rays in the connecting portion can be prevented.

(Mechanism for Transporting Test-Subject Table)

In FIGS. 3 and 5, a slider 51 is provided as a third table transporting mechanism to the interior of the second casing 24. A first table transporting mechanism 52 is housed inside the slider 51. A test-subject table 53 is placed on the slider 51, and this test-subject table is linked to the first table transporting mechanism 52. The first table transporting mechanism 52 causes the test-subject table 53 to move in a horizontal direction, i.e., to move in a slidable fashion.

The test-subject table 53 has a curved shape that is downwardly convex in cross section (i.e., the surface for receiving a test subject S is concave), which is a so-called trough shape. The test-subject table 53 is formed in the present embodiment using a translucent material, i.e., a material in which the underside can be seen through. However, it is also acceptable to form the test-subject table 53 using an opaque material.

The test subject S, which is the object of a CT measurement, is placed on the test-subject table 53. The test subject S is, for example, a relatively large animal such as a dog, a cat, or the like, or a relatively small animal such as a bird, a rabbit, a lizard, or the like. An animal other than a dog or a cat may be called an exotic animal. Although the animal, which is the test subject 5, is easy to stabilize and set down on the test-subject table 53 because the test-subject table 53 has a trough shape, the test subject S can be anesthetized using an anesthetic drug in a case in which the test subject S does not remain docile during measurement.

The first table transporting mechanism 52 may be configured using a well-known horizontal motion mechanism. Such a horizontal motion mechanism may be configured to include, for example, a motor 54 having a controllable rotation angle, such as a servomotor, a pulse motor, or the like; and a lead screw (not shown) driven by the motor 54 and rotating about its own center axis line. The motor 54 is connected to the CPU 11 in the control device 3 through the controller 42 in FIG. 1.

Figure 9:
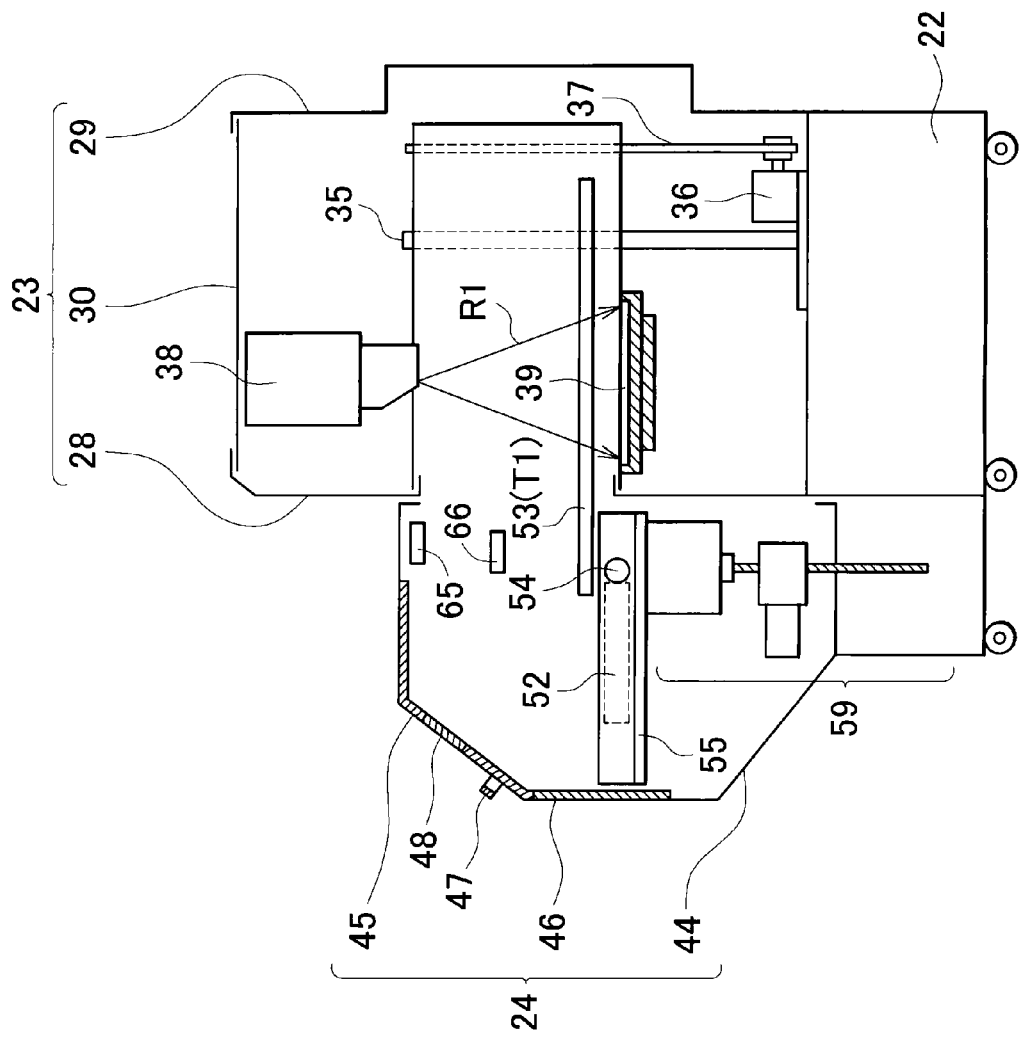
FIG. 9 is a cross-sectional view showing yet another usage configuration of the CT measurement system shown in FIG. 2.

The test-subject table 53 is driven by the first table transporting mechanism 52, and moves horizontally between the first table position T1, which is a position where the main portion of the test-subject table 53 receives an X-ray R1 coming out of the X-ray generator 38 as shown in FIG. 9, and the second table position T2, which is a position where the main portion of the test-subject table 53 is on the outside of the first casing 23 as shown in FIG. 3.

Figure 6:
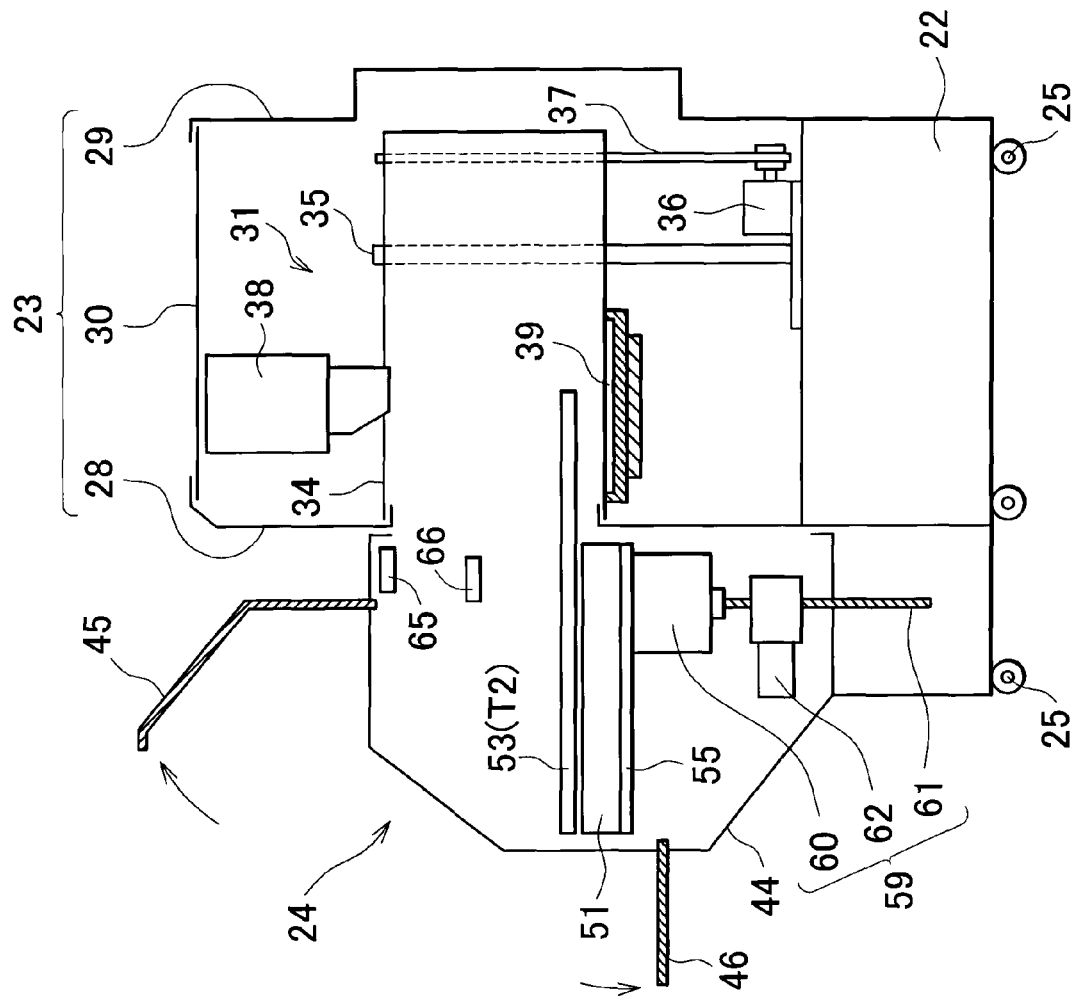
FIG. 6 is a cross-sectional view of the CT measurement system shown in FIG. 5.
Figure 8:
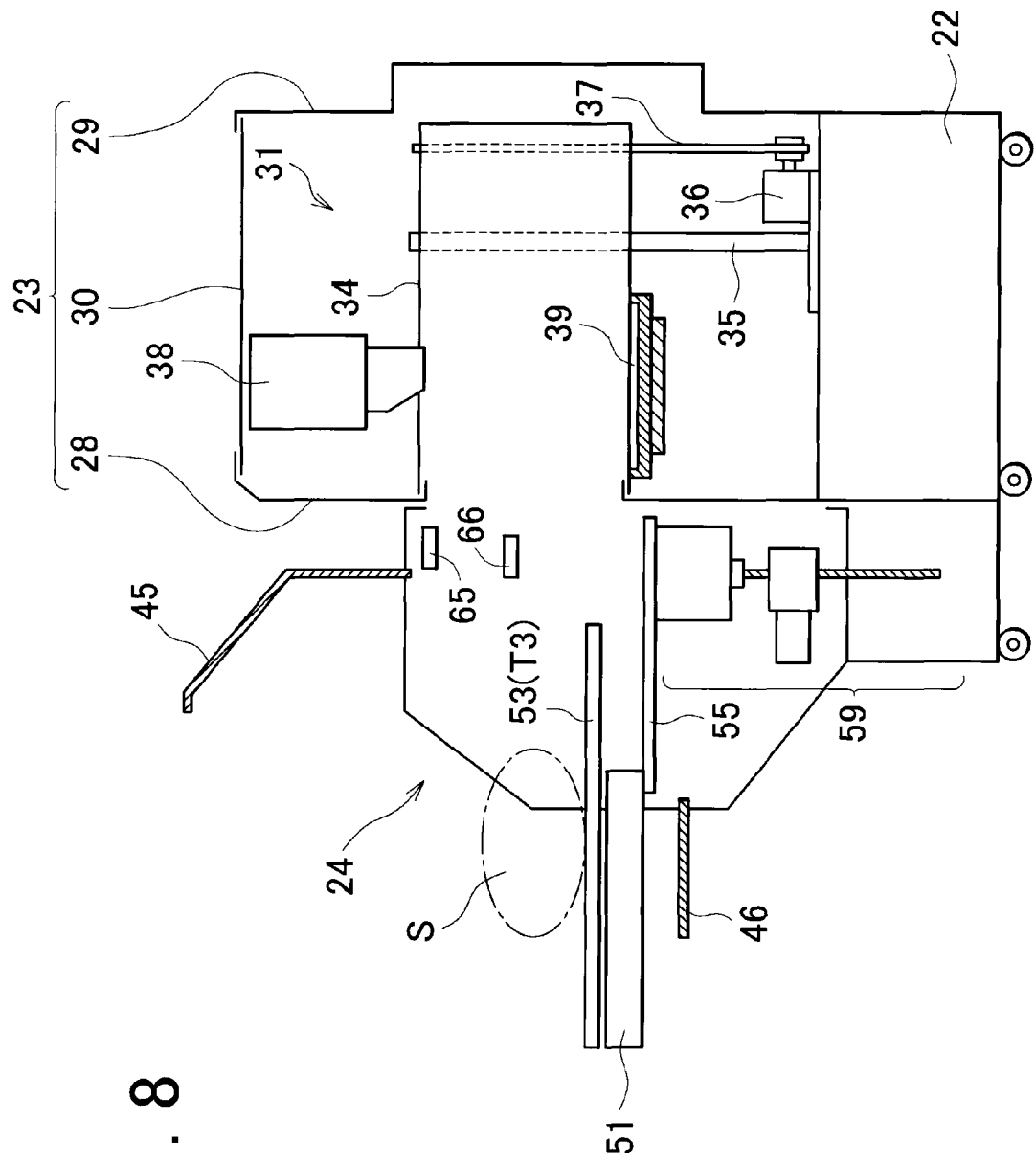
FIG. 8 is a cross-sectional view of the CT measurement system shown in FIG. 7.

In FIG. 3, the slider 51 is placed on a rail 55. The slider 51 can thereby be manually moved horizontally along the rail 55. As shown in FIG. 5, a handle 56 which the measurer can pull with a finger is provided on the front surface of the slider 51. Specifically, the slider 51 may be slidably moved between a position where the test-subject table 53 is placed in the second table position T2 as shown in FIG. 6, and a position where the test-subject table 53 is placed in a third table position T3 as shown in FIG. 8. The third table position T3 is a position in which the main portion of the test-subject table 53 is even farther from the first casing 23 than the second table position T2 shown in FIG. 6.

In FIG. 3, the rail 55 is supported by a second table transporting mechanism 59. The second table transporting mechanism 59 has: a hoist block 60 fixed to the rail 55; a lead screw shaft 61 in threadable engagement with the hoist block 60; and a motor 62 for rotating the lead screw shaft 61 about its own center line. The motor 62 is fixedly installed either in the main casing unit 44 of the second casing 24 or in an auxiliary casing 63 that extends downward from the bottom surface of the main casing unit 44 as shown in FIG. 2. The lower part of the lead screw shaft 61 enters the interior of the auxiliary casing 63. The motor 62 is a motor having a controllable rotation angle, for example, a servomotor or a pulse motor. The motor 62 is connected to the CPU 11 in the control device 3 through the controller 42 in FIG. 1.

(Method of Arranging Test Subject)

The operation of the X-ray CT apparatus 1 thus configured is described hereinbelow.

In a case in which the X-ray CT apparatus 1 of FIG. 1 is in a standby state, the CT measurement system 2 is in the state shown in FIGS. 2 and 3, i.e., the upper door 45 and the lower door 46 are closed, and the test-subject table 53 is in the second table position T2.

In a case in which the test subject S is a small animal, for example, a bird, a mouse, or the like, the measurer raises the upper door 45 upward from the state in FIG. 2 and forms an aperture in the upper part of the second casing 24. The measurer then inserts the small test subject S into the second casing 24 through the aperture, and places the test subject S on the test-subject table 53.

In a case in which the test subject S is an animal of about medium size, for example, a young cat or a young dog, and merely opening the upper door 45 leaves the aperture small and difficult to insert the test subject S through, the measurer opens both the upper door 45 and the lower door 46, as shown in FIGS. 5 and 6. The front surface of the second casing 24 is thereby widely opened. The measurer inserts the medium-sized test subject S into the second casing 24 through the large aperture, and places the test subject S on the test-subject table 53.

Figure 7:
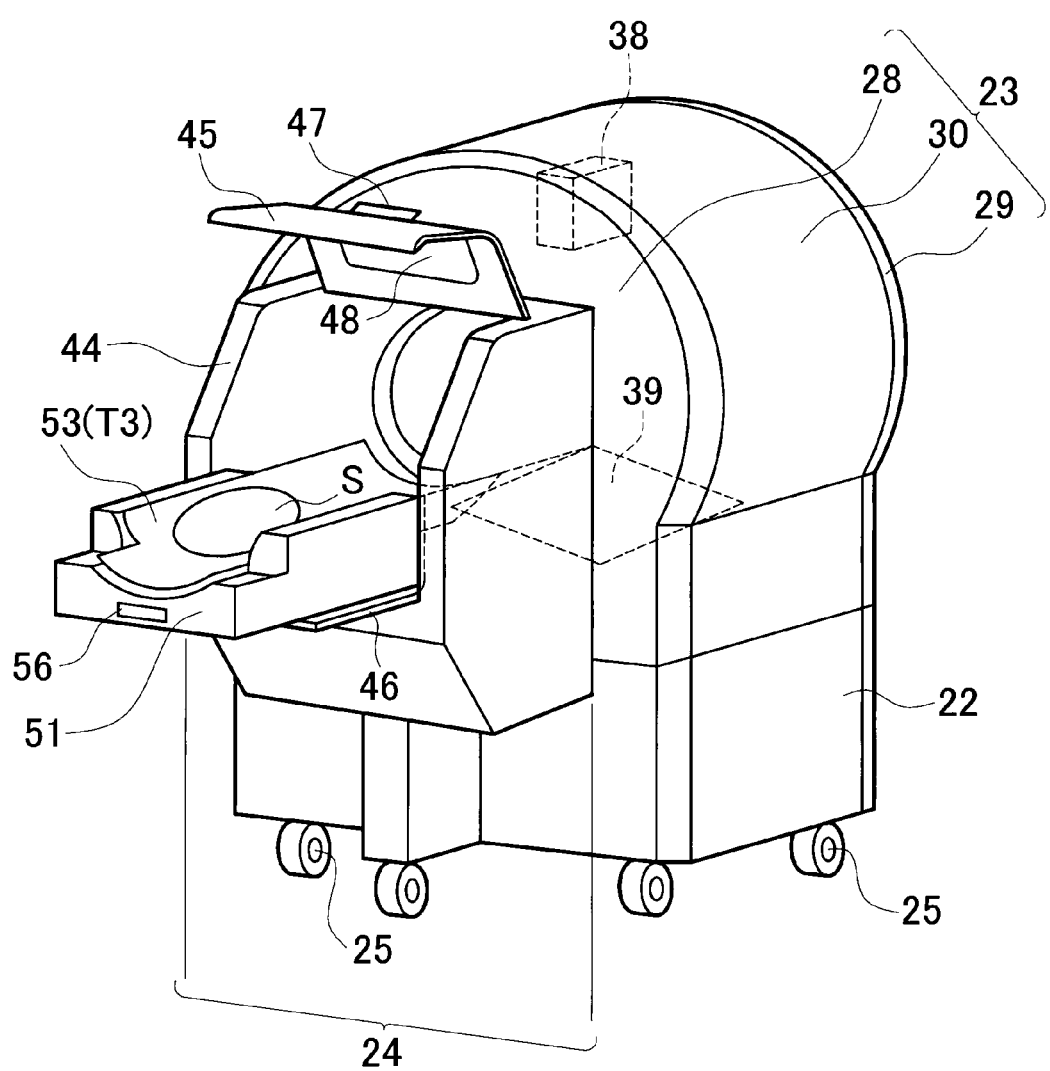
FIG. 7 is a perspective view showing another usage configuration of the CT measurement system shown in FIG. 2.

In a case in which the test subject S is a large animal, for example, an adult cat or an adult dog, and merely opening both the upper door 45 and the lower door 46 leaves the aperture small and difficult to insert the test subject S through, the measurer pulls the handle 56 with a finger and pulls out the slider 51 to a specific distance in front of the second casing 24, as shown in FIGS. 7 and 8. The test-subject table 53 is thereby pulled out to the third table position T3. The upper region of the test-subject table 53 is thereby brought to a widely opened state, and the measurer can place the large-sized test subject S on the test-subject table 53 without difficulty.

(Method of Transporting Test Subject and Method of CT Measurement)

In a case in which the test-subject table 53 is in a pulled-out state in the third table position T3, which is a position in front of the second casing 24 as shown in FIG. 7, and the measurer has placed the test subject S on the test-subject table 53, the measurer then pushes the test-subject table 53 toward the first casing 23 and places the test-subject table 53 in the second table position T2 inside the second casing 24 as shown in FIGS. 5 and 6. The measurer then closes the upper door 45 and the lower door 46 and places them in the state shown in FIG. 3. In a case in which the measurer has placed the test subject S on the test-subject table 53 while the test-subject table 53 is in the second table position T2, the measurer then closes the upper door 45 and the lower door 46 and places them in the state shown in FIG. 3. The measurer can observe the condition of the test subject S through the window 48 when the doors are in this state.

The CPU 11 in FIG. 1 subsequently adjusts the vertical position (i.e., height) of the test-subject table 53 using the second table transporting mechanism 59 in FIG. 3 in accordance with the instructions of the CT measurement software 19. This adjustment will hereinafter be described in detail. The CPU 11 then applies a high voltage to the X-ray generator 38 to start the generation of X-rays, and operates the first table transporting mechanism 52 in FIG. 3 to move the test-subject table 53 horizontally from the second table position T2 to the first table position T1 shown in FIG. 9. The measurer can observe the condition of the test subject S being transported. The test subject is observed through the window 48 while the test-subject table 53 is moving.

The X-rays emitted from the X-ray generator 38 are irradiated on the test subject S on the test-subject table 53 while the test-subject table 53 moves from the second table position T2 in FIG. 3 to the first table position T1 in FIG. 9. The X-rays that have passed through the test subject S are detected by the two-dimensional X-ray detector 39 at this time. The two-dimensional X-ray detector 39 detects the X-rays in individual pixel regions within a two-dimensional region. The X-ray intensity calculation device 49 of FIG. 1 determines the X-ray intensity by calculation on the basis of the output signal of the two-dimensional X-ray detector 39, and transmits the intensity information to the control device 3 in the form of an electrical signal.

The X-ray intensity data transmitted from the X-ray intensity calculation device 49 is stored in the data file 20 in the memory 14 as necessary, and is transmitted to the video controller 18 as necessary. The video controller 18 generates an image signal in accordance with the transmitted X-ray intensity data, and transmits the image signal to the image display device 4. An X-ray cross-sectional image of the test subject S is thereby displayed on the screen of the image display device 4. The measurer may observe the condition of the test subject S, which is being irradiated by the X-rays, through the window 48 while the measurement is being performed.

When the measurement is completed, the CPU 11 completes the X-ray emission from the X-ray generator 38, and operates the first table transporting mechanism 52 in FIG. 9 to transport the test-subject table 53 from the first table position T1 to the second table position T2 in FIG. 3. The measurer then opens the upper door 45, opens the lower door 46 as necessary, manually pulls out the slider 51 to the third table position T3 in FIG. 7 as necessary, and takes out the completely measured test subject S from the test-subject table 53.

(Adjusting the Height of Test Subject)

In FIG. 3 in the present embodiment as described above, the height of the test subject S is adjusted using the second table transporting mechanism 59 before the CT measurement is performed using the X-rays emitted from the X-ray generator 38. The term "adjusting the height of the test subject S" means adjusting the distance of the test subject S from the X-ray generator 38, i.e., adjusting the distance of the test subject S from the center line of rotation X0 of the X-ray generator 38 and the X-ray detector 39.

As stated previously, the test subject S is sometimes a small animal such as a bird, a medium-sized animal such as a young dog, or a large animal such as an adult dog. When the test subject S varies between small, medium, and large sizes while the height of the test-subject table 53 remains constant, there is a concern that the center position of the test subject S in relation to the X-ray R1 will fluctuate and variations in measurement results will be generated. In order to prevent such generation of variations in measurement results, the center position of the test subject S in relation to the X-ray R1 (i.e., the distance of the test subject S from the X-ray generator 38) is adjusted in the present embodiment so as to remain constant by varying the vertical position of the test-subject table 53 in a case in which test subjects S are provided in differing sizes. Because there are several specific methods, they will be explained individually.

1. Storing in Advance a Height Position that Corresponds to the Size of Test Subject The height position in which the test-subject table 53 is to be placed in correspondence with the size of the test subject S is determined experientially. In a first embodiment, information about the height position of the test-subject table 53 that corresponds with the size of the test subject S is stored in advance in the CT measurement software 19 of FIG. 1 or a specific memory region within the memory 14. When the size of the test subject S is determined, the second table transporting mechanism 59 in FIG. 3 is operated to adjust the vertical position (i.e., height position) of the test-subject table 53.

2. Using Preliminary Measurement by Laser Pointer

A laser pointer is a laser device for radiating a laser light of a specific cross-sectional shape toward an object. A laser pointer 65 for irradiating the test subject S with the laser light from upside and a laser pointer 66 for irradiating the test subject S with the laser light in the lateral direction are both arranged in a suitable location in front of the first casing 23 in FIG. 3. And they radiate the laser light in a given position on the center portion of the X-ray R1. When the test subject S placed on the test-subject table 53 reaches the irradiation region of the X-ray R1, the point of the laser light appears on the surface of the test subject S. The measurer can observe this effect through the observation window 48 provided to the upper door 45 of the second casing 24 in FIG. 2.

The measurer, having seen the point display of the laser light that appears on the surface of the test subject S, can evaluate and confirm by sight the distance by which the test subject S deviates above or below the optimal height position on the basis of the point display. The measurer can input data for adjusting the height by using the input device 5 in FIG. 1 on the basis of the confirmation result. The CPU 11 operates the second table transporting mechanism 59 in FIG. 3 on the basis of the input data, and can establish a suitable position for the height position of the test-subject table 53.

3. Using Preliminary Measurement by Fluoroscopy

Before an actual measurement is performed in FIG. 3, the test subject S placed on the test-subject table 53 is arranged within the irradiation region of the X-ray R1 by moving the test-subject table 53. A measurement is performed using the X-ray detector 39, and a CT X-ray cross-sectional image is displayed on the screen of the image display device 4. The measurer, having seen the image, evaluates whether the test subject S is too high or too low in relation to the X-ray R1 on the basis of the displayed cross-sectional image.

The measurer may input data for adjusting the height by using the input device 5 in FIG. 1 on the basis of the evaluation result. The CPU 11 operates the second table transporting mechanism 59 in FIG. 3 on the basis of the input data, and can establish a suitable position for the height position of the test-subject table 53. On the basis of the fluoroscopic data, the CPU 11 can automatically measure the physical thickness of the test subject S, automatically adjust the height of the test-subject table, and automatically establish a suitable imaging dose for CT imaging.

Effects of the Present Embodiment

In the present embodiment as described above, the measurer can set (i.e., arrange) and remove the test subject S on and from the test-subject table 53 in the second table position T2, which is a position outside the first casing 23, because the first table transporting mechanism 52 in FIG. 9 is configured to transport the test-subject table 53 between the first table position T1 (FIG. 9), which is a position for receiving X-rays, and the second table position T2 (FIG. 3), which is a position outside the first casing 23. Further, the test subject S on the test-subject table 53 is placed consistently and precisely in the first table position T1 by the action of the first table transporting mechanism 52.

Therefore, the task of setting the test subject S in a specific position inside the first casing 23 may be performed more simply, more quickly, and more precisely according to the present embodiment than with the conventional CT apparatus, in which the test subject S is arranged inside the casing through an aperture that becomes visible after the door provided to a side surface of the casing is opened.

Moreover, because the height position of the test-subject table 53 (i.e., the distance of the test-subject table 53 from the X-ray generator 38) is adjusted in the present embodiment by the second table transporting mechanism 59, it is possible to place the test subject S consistently in a given position in relation to the X-ray R1 even in a case in which test subjects S are provided in varying sizes. A consistently stable, highly reliable CT measurement can thereby be performed on test subjects S of differing sizes.

Other Embodiments

Although a preferred embodiment was presented to describe the present invention above, the present invention is not limited to this embodiment; various alterations can be made within the scope of the invention as set forth in the claims.

For example, the first table transporting mechanism 52 and the second table transporting mechanism 59 in FIG. 3 are not limited to transporting mechanisms configured as shown in FIG. 3, but rather can make use of any other transporting mechanism. Once the configurations of the first table transporting mechanism 52 and the second table transporting mechanism 59 are altered, the configuration of the control system in FIG. 1 may also be altered accordingly.

The exterior shapes of the first casing 23 and the second casing 24 shown in FIG. 2 are not limited to the exterior shapes shown in FIG. 2, but rather can be various other exterior shapes.

In FIG. 5 in the above embodiment, the upper door 45 as a first door is configured so as to move to open upward, and the lower door 46 as a second door is configured so as to move to open downward. However, the first door may instead be configured so as to move to open in a direction other than upward (for example, toward the left), and the second door may be configured so as to move to open in the opposite direction (for example, toward the right). The first door and the second door may also be configured so as to move open and closed in a diagonal direction.

In FIG. 3, the CT measurement system 2 may have a sensor for detecting the open or closed state of the upper door 45, a sensor for detecting the open or closed state of the lower door 46, and a supply-blocking circuit for blocking off the power supply to the X-ray generator 38. According to this embodiment, in a case in which the upper door 45 and/or the lower door 46 is mistakenly opened during X-ray radiation, the open state can be detected by the sensors, and the power supply to the X-ray generator 38 can be blocked off by the supply-blocking circuit on the basis of the detection result. Exposure of the measurer to X-rays can thereby be prevented, i.e., the safety of the measurer in relation to the X-rays can be ensured.

In FIG. 3, the lower door 46 may be configured so as to be unable to open when the upper door 45 is not open, and a blocking mechanism can be provided to prevent the upper door 45 from being opened from a closed state to an opened state. This blocking mechanism may be configured using, for example, a solenoid, which is a magnetic movable mechanism. According to this embodiment, the unintentional opening of the upper door 45 and the lower door 46 can be prevented by placing the upper door 45 in a blocked state using the blocking mechanism. As a result, the safety of the measurer in relation to X-rays can be ensured.

In the above-described embodiments, the laser pointer means is constituted by two laser pointers 65 and 66. However, the laser pointer means may instead be constituted by single laser pointer or three or more laser pointers.

KEY TO SYMBOLS

1. X-ray CT apparatus, 2. CT measurement system, 3. control device, 4. image display device, 5. input device, 6. keyboard, 7. mouse, 15. bus, 18. video controller, 19. CT measurement software, 22. base, 23. first casing, 24. second casing, 25. caster, 28. front-surface plate, 29. back-surface plate, 30. drum plate, 31. CT optical system, 34. rotating drum, 35. supporting member, 36. motor, 37. belt (power transmitting means), 38. X-ray generator, 39. two-dimensional X-ray detector, 41. X-ray emission window, 42. controller, 44. main casing unit, 45. upper door (first door), 46. lower door (second door), 47. handle, 48. window, 51. slider (third table transporting mechanism), 52. first table transporting mechanism, 53. test-subject table, 54. motor, 55. Rail, 56. handle, 59. second table transporting mechanism, 60. hoist block, 61. lead screw shaft, 62. motor, 63. auxiliary casing, 65. first laser pointer, 66. second laser pointer, B. connecting portion between first casing and rotating drum, C. connecting portion between first casing and second casing, R1. X-ray, X0. center axis line, P0. lead plate, T1. first table position, T2. second table position, T3. third table position

What is claimed is:

1. An X-ray CT apparatus for obtaining an internal image of a test subject by using X-rays;
   the X-ray CT apparatus comprising:
   X-ray generation means for generating X-rays irradiated on the test subject;
   X-ray detection means for detecting X-rays that have passed through the test subject;
   rotary drive means for simultaneously rotating the X-ray generation means and the X-ray detection means about a center line of rotation;
   a first casing for enclosing the X-ray generation means and the X-ray detection means;
   a test-subject table on which the test subject is placed;
   a first table transporting mechanism for transporting the test-subject table between a first table position and a second table position, the first table position being a position where the main portion of the test-subject table receives the X-rays generated by the X-ray generation means, and the second table position being a position where the main portion of the test-subject table is on the outside of the first casing;
   a second table transporting mechanism for transporting the test-subject table closer to or farther from the center line of rotation of the X-ray generation means and the X-ray detection means;
   means whereby the test-subject table on which the test subject is placed is transported from the second table position to the first table position by the first table transporting mechanism; and
   means whereby the distance of the test subject from the center line of rotation of the X-ray generation means and the X-ray detection means is varied by the second table transporting mechanism in accordance with the size of the test subject.

2. The X-ray CT apparatus according to claim 1, further comprising:
   a second casing for enclosing the second table position; and
   the second casing having a pair of doors that move open or closed in order to open up or close off a path on which the test-subject table is transported by the first table transporting mechanism.

3. The X-ray CT apparatus according to claim 2, wherein a window for observing the interior is provided to at least one of the pair of doors.

4. The X-ray CT apparatus according to claim 1, further comprising:
   laser pointer means for indicating a position by laser light;

a window provided to the first casing or the second casing in order to observe the position indicated by the laser pointer means;

input means for inputting data; wherein the means for varying the distance of the test subject varies the distance of the test subject from the center line of rotation of the X-ray generation means and the X-ray detection means by the second table transporting mechanism in accordance with the data input from the input means.

5. The X-ray CT apparatus according to claim 1, further comprising:

input means for inputting data;

means whereby the distance of the test subject in relation to the center line of rotation of the X-ray generation means and the X-ray detection means is determined by X-ray fluoroscopy; wherein the means for varying the distance of the test subject varies the distance of the test subject from the center line of rotation of the X-ray generation means and the X-ray detection means by the second table transporting mechanism in accordance with the data determined by X-ray fluoroscopy.

6. The X-ray CT apparatus according to claim 1, further comprising a third table transporting mechanism for transporting the test-subject table to a third table position, which is a position even farther from the first casing than the second table position.

7. The X-ray CT apparatus according to claim 1, wherein the test-subject table has a curved cross-sectional shape in which the surface for receiving the test subject is recessed.

* * * * *